United States Patent
Cooper et al.

(10) Patent No.: US 10,288,619 B2
(45) Date of Patent: May 14, 2019

(54) BIOMARKERS FOR HUMAN MONOCYTE MYELOID-DERIVED SUPPRESOR CELLS

(71) Applicant: CASE WESTERN RESERVE UNIVERSITY, Cleveland, OH (US)

(72) Inventors: Kevin D. Cooper, Cleveland, OH (US); Thomas S. McCormick, Cleveland, OH (US); David S. Soler, Cleveland, OH (US); Andrew Young, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/321,894

(22) PCT Filed: Jun. 24, 2015

(86) PCT No.: PCT/US2015/037495
§ 371 (c)(1),
(2) Date: Dec. 23, 2016

(87) PCT Pub. No.: WO2015/200524
PCT Pub. Date: Dec. 30, 2015

(65) Prior Publication Data
US 2017/0192006 A1    Jul. 6, 2017

Related U.S. Application Data

(60) Provisional application No. 62/016,283, filed on Jun. 24, 2014.

(51) Int. Cl.
| | | |
|---|---|---|
| *C12Q 1/68* | (2018.01) | |
| *G01N 33/574* | (2006.01) | |
| *G01N 33/564* | (2006.01) | |
| *C12N 15/113* | (2010.01) | |
| *C12Q 1/6886* | (2018.01) | |
| *A61K 31/70* | (2006.01) | |

(52) U.S. Cl.
CPC ..... *G01N 33/57484* (2013.01); *C12N 15/113* (2013.01); *C12Q 1/6886* (2013.01); *G01N 33/564* (2013.01); *G01N 33/57488* (2013.01); *C12N 2310/14* (2013.01); *C12Q 2600/136* (2013.01); *C12Q 2600/158* (2013.01); *G01N 2800/50* (2013.01)

(58) Field of Classification Search
None
See application file for complete search history.

(56) References Cited

U.S. PATENT DOCUMENTS

2011/0027275 A1    2/2011   Ferrara et al.
2013/0165337 A1*   6/2013   Robinson ............. C12Q 1/6837
                                                              506/9
2013/0165343 A1    6/2013   Robinson et al.

FOREIGN PATENT DOCUMENTS

WO    2013162773 A1    10/2013

* cited by examiner

*Primary Examiner* — Sean McGarry
(74) *Attorney, Agent, or Firm* — Tarolli, Sundheim, Covell & Tummino LLP

(57) ABSTRACT

A method for diagnosing an increased risk of a cancer in a subject includes the steps of obtaining a blood sample from the subject and determining, in the blood sample, a level of two or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3, wherein an increase in the level of two or more of the polypeptides compared to a control level is indicative of an increased risk of cancer in the subject.

7 Claims, 8 Drawing Sheets

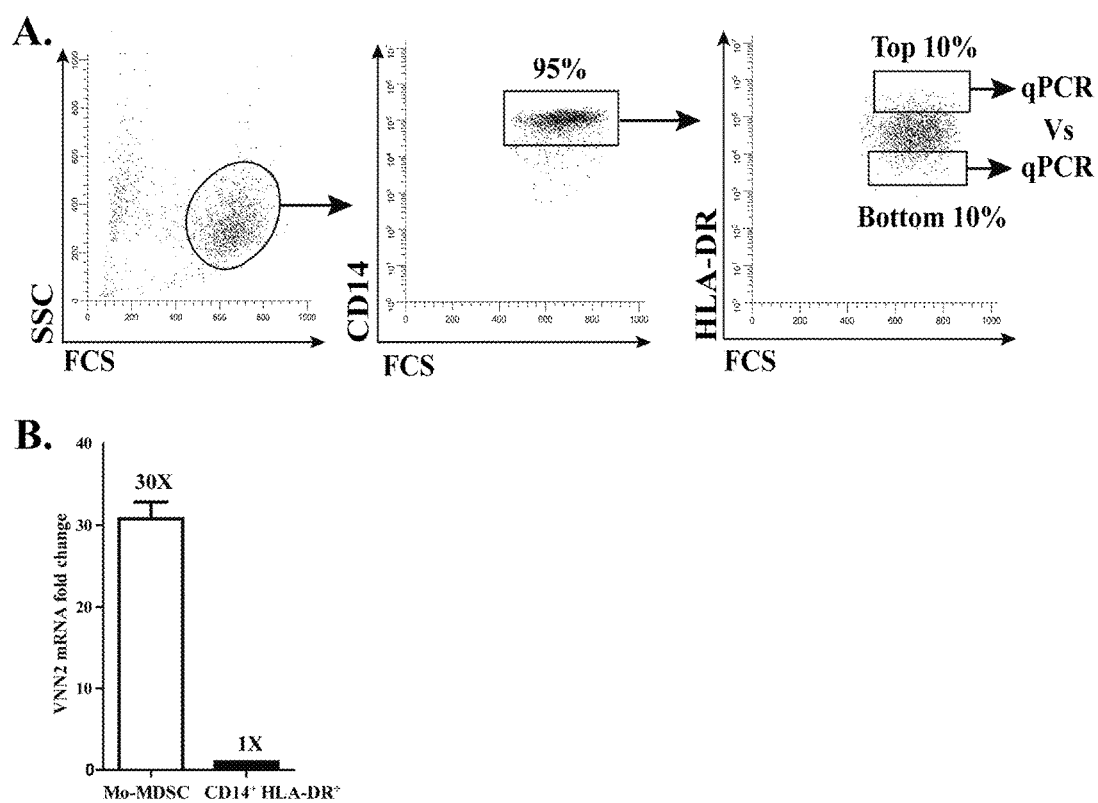
Figs. 1A-B

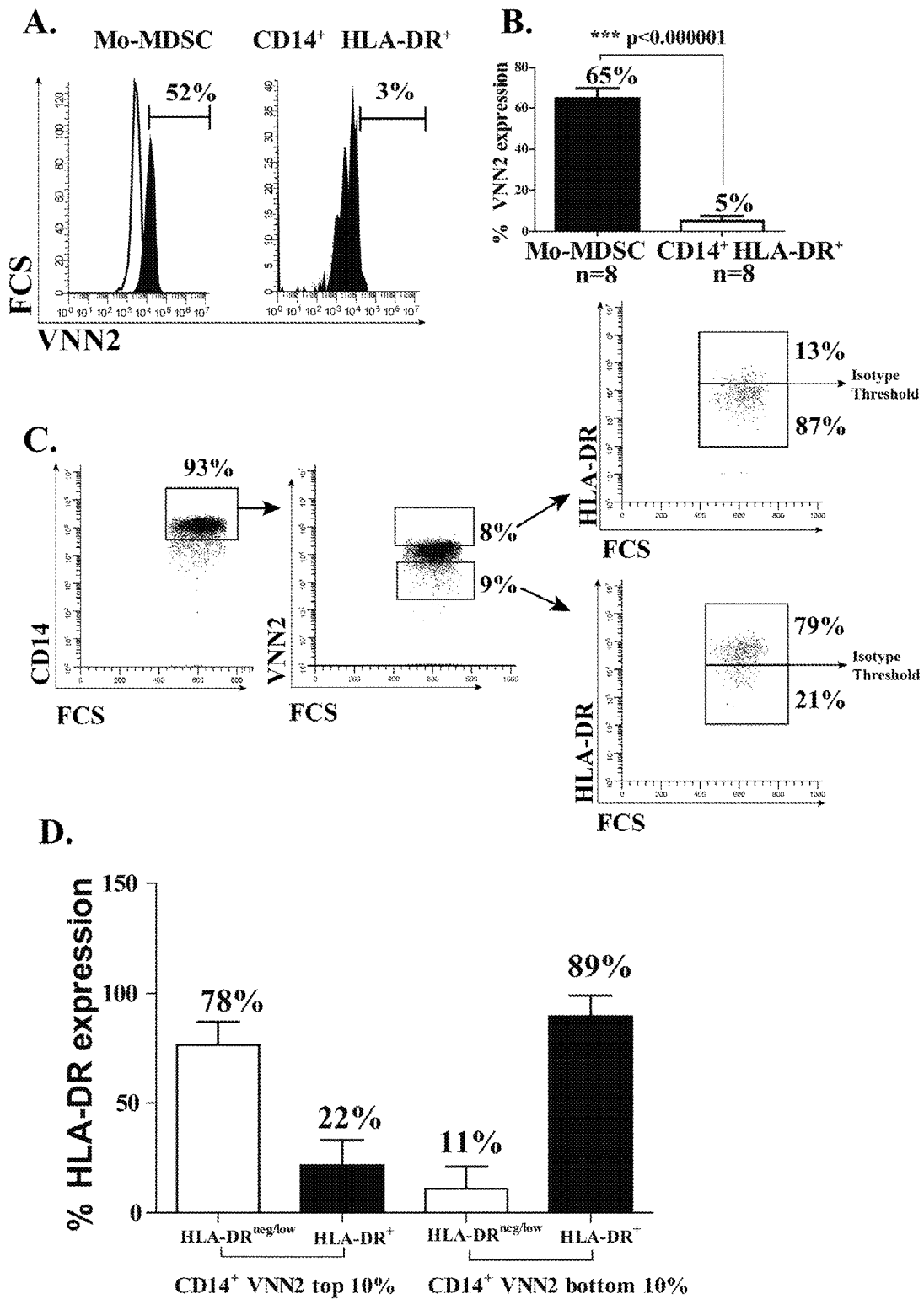
Figs. 2A-D

A.
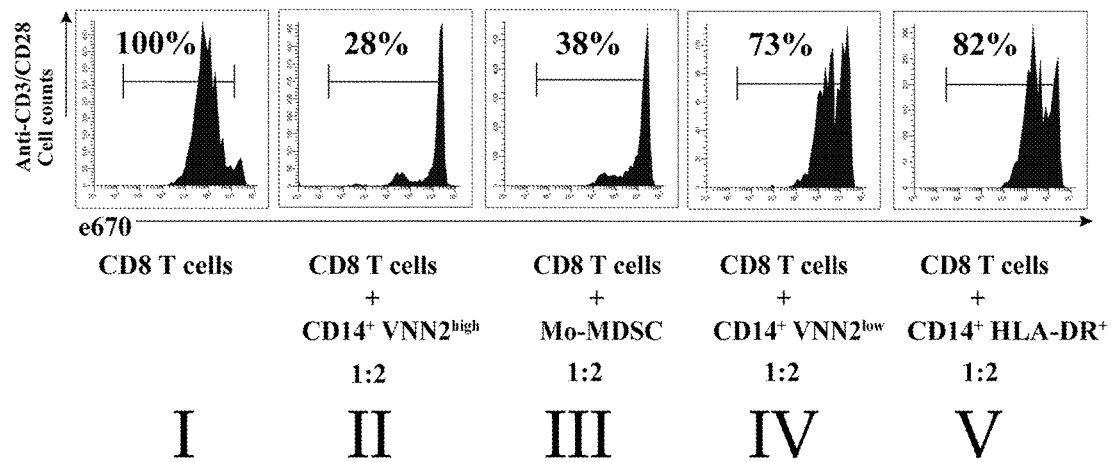
B.
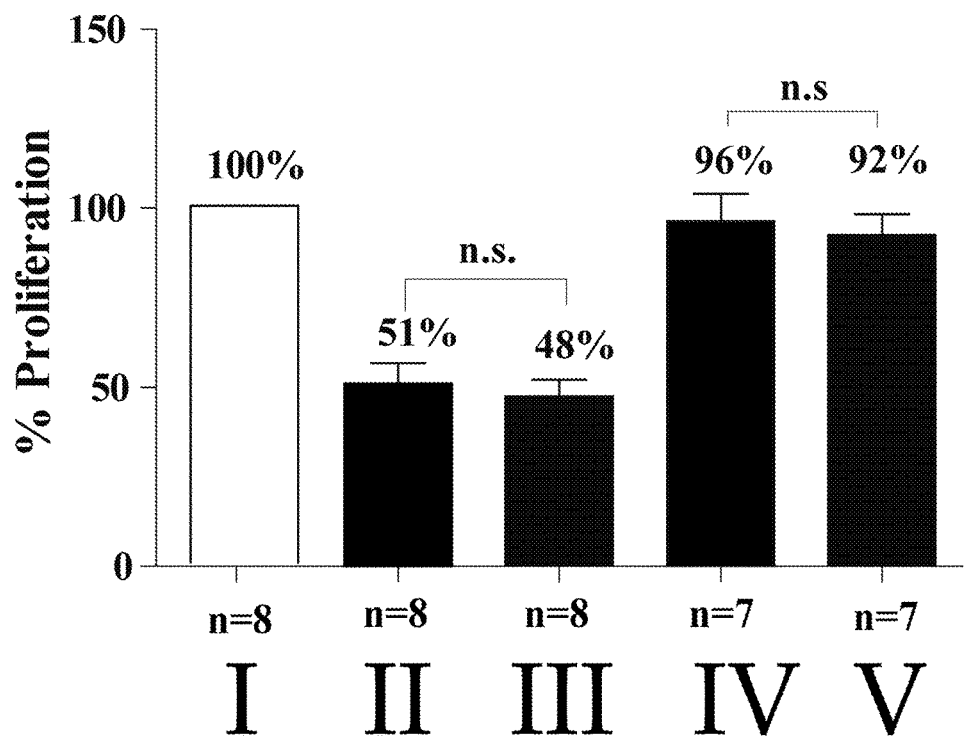
Figs. 3A-B

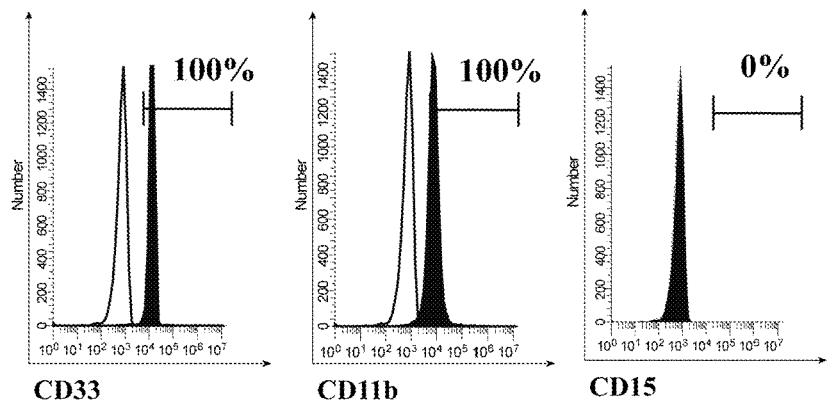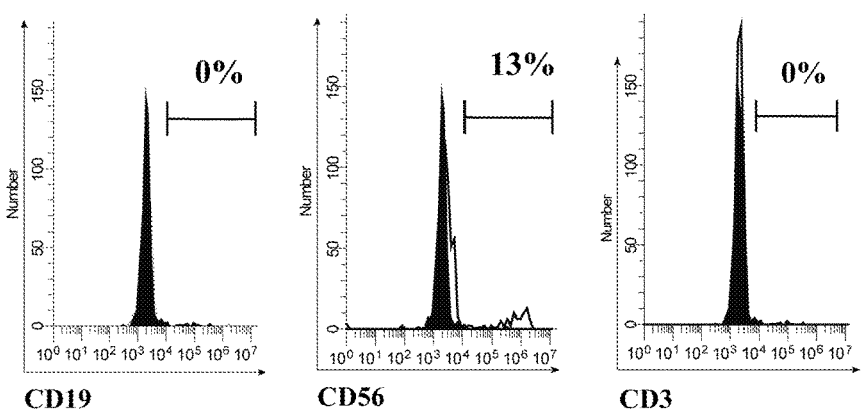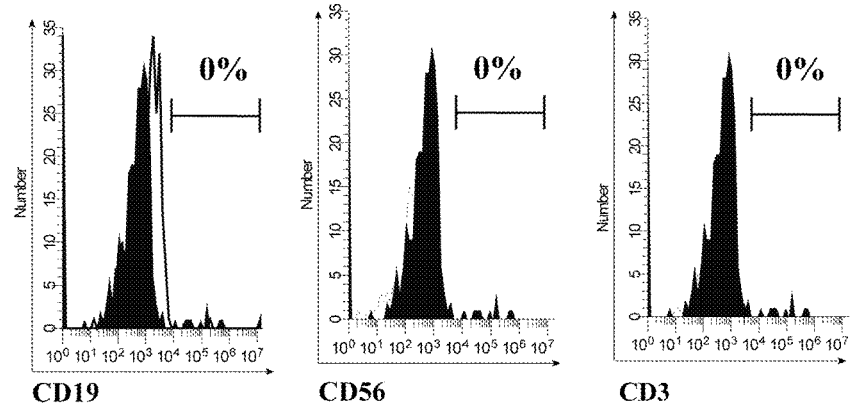
Figs. 4A-C

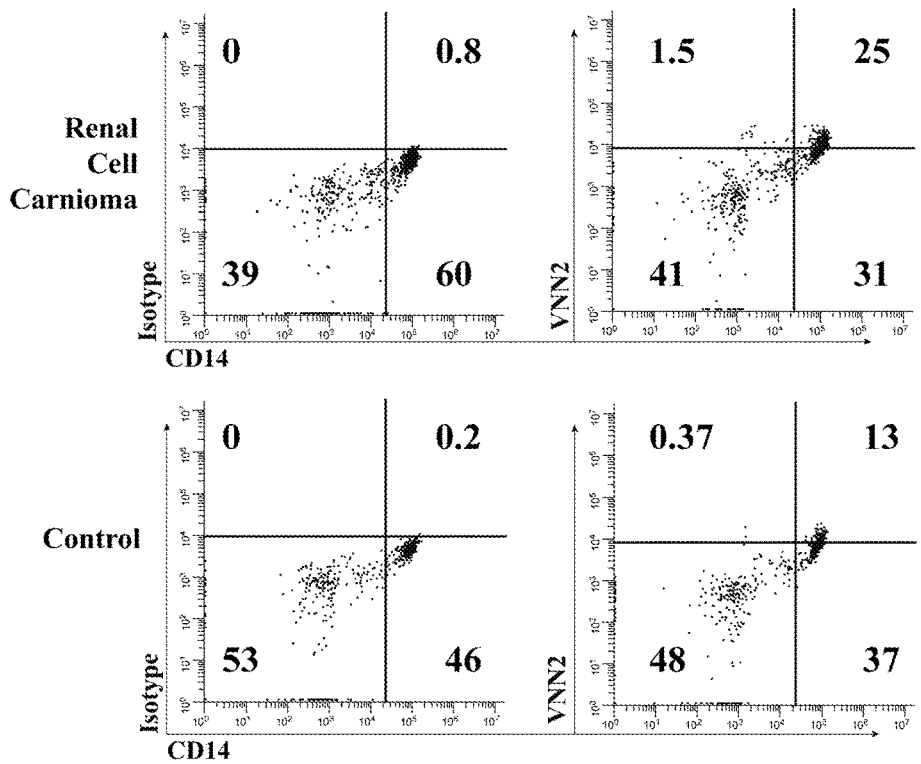
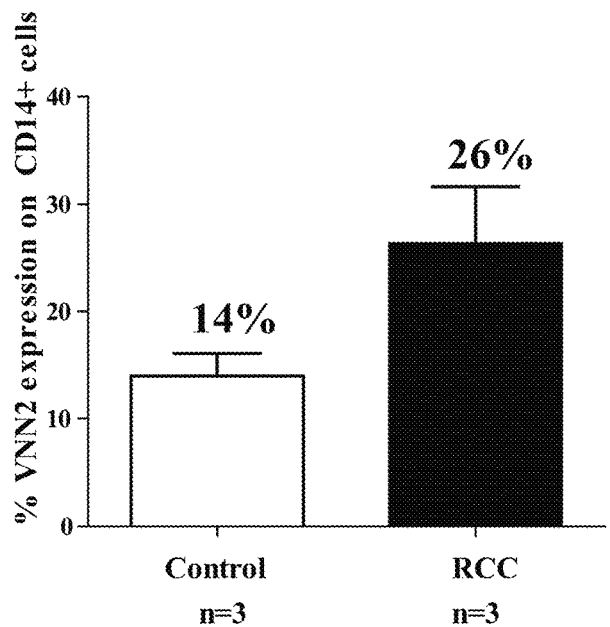
Figs. 5A-B

BIOMARKERS FOR HUMAN MONOCYTE MYELOID-DERIVED SUPPRESOR CELLS

RELATED APPLICATION

This application claims priority from U.S. Provisional Application No. 62/016,283, filed Jun. 24, 2014 the subject matter of which is incorporated herein by reference in tits entirety.

GOVERNMENT FUNDING

This invention was made with government support under Grant Nos. AR039750 and AR051498 awarded by The National Institutes of Health. The United States government has certain rights to the invention.

BACKGROUND

Myeloid Derived Suppressor Cells (MDSCs) represent an intrinsic part of the myeloid-cell lineage that were initially described in cancer patients more than two decades ago. MDSC consist of a heterogeneous population of immature cells that expand during cancer, inflammation and infection. In particular, human MDSC are currently classified into granulocytic $CD33^+$, $CD15^+$, $CD14^{neg}$, $CD11b^+$, $HLA-DR^{neg/low}$ (G-MDSC) or monocytic $CD33^+$, $CD11b^+$, $CD14^+$, $CD15^{neg}$, $HLA-DR^{neg/low}$ (M-MDSC) sub-populations.

Monocytes are produced in the bone-marrow, and in healthy individuals they quickly differentiate into mature granulocytes, macrophages or dendritic cells (DC). However, under chronic inflammatory conditions such as in cancer, monocyte differentiation can be blocked which results in an expanded M-MDSC population found in peripheral blood. Currently the only approach to specifically isolate M-MDSCs is to islote $CD14^+$ cells with low expression of HLA-DR and test if they can functionally suppress proliferation. However, the absence of positive markers specific for human M-MDSC leads to delays in the characterization and in-tissue study of this heterogeneous immunosuppressive cell population.

BRIEF DESCRIPTION OF DRAWINGS

The accompanying drawings, which are incorporated in and constitute a part of this specification, illustrate some embodiments disclosed herein, and together with the description, serve to explain principles of the exemplary embodiments disclosed herein.

FIGS. 1(A-B) illustrate that VNN2 mRNA is highly enriched in M-MDSC. A) represents a schematic representation of how the M-MDSC are sorted and analyzed for qPCR. B) VNN2 qPCR showing that VNN2 mRNA is enriched 30-fold in M-MDSC compared to $CD14^+$ $HLA-DR^+$ cells. Data is representative of two independent experiments.

FIGS. 2(A-D) illustrate high VNN2 surface protein-expressing $CD14^+$ cells are enriched in $CD14^+$ $HLA-DR^{neg/low}$ cells of M-MDSC phenotype. A) Representative flow cytometry plot showing human M-MDSC express 52% of VNN2 protein compared to 3% expression in $CD14^+$ $HLA-DR^+$ cells (top 10% HLA-DR monocytes), relative to their respective isotype control staining. B) Average percentage of cells expressing VNN2 protein in M-MDSC compared to $CD14^+$ $HLA-DR^+$ cells (65% vs. 5%, n=8 each, p>0.000001). C) Representative flow cytometry plot showing $CD14^+$ $VNN2^{high}$ cells express low HLA-DR compared to high HLA-DR expression among $CD14^+$ $VNN2^{low}$ cells. D) Increasing mean HLA-DR values in top 10%-expressing VNN2 cells, top 20-40% VNN2-expressing cells, 60-80% VNN2-expressing cells and bottom 10% VNN2-expressing cells.

FIGS. 3(A-B) illustrate that $CD14^+$ $VNN2^{high}$, but not $CD14^+$ $VNN2^{neg}$ cells, suppress CD8 T cells with similar effectiveness to that of $CD14^+$ $HLA-DR^{neg/low}$ traditional MDSC. A) Representative functional suppression assay. Panel I) CD8 T cells loaded with e670 demonstrate dye dilution upon proliferation after stimulation with anti-CD2/CD3/CD28 beads. Panel II) and III) show suppression of proliferation of CD8 T cells by $CD14^+$ $VNN2^{high}$ cells (panel II) equals that of M-MDSC (panel III). Panels IV) and V) CD8 T cell proliferation is not suppressed in co-cultures with either $CD14^+$ $VNN2^{low}$ or $CD14^+$ $HLA-DR^+$ cells respectively.

FIGS. 4(A-C) illustrate that $CD14^+$ $VNN2^{high}$ cells are lineage negative for B-cells, NK-cells and T-cells. A) The magnetically bead-enriched $CD14^+$ cells stained 100% positive for $CD33^+$ and $CD11b^+$ while being negative for CD15 expression. B) $VNN2^{high}$ (top 10%) cells and C) $HLA-DR^{low/neg}$ cells stained from the $CD14^+$ magnetically-enriched cells were $CD19^{neg}$, $CD56^{neg}$ and $CD3^{neg}$.

FIGS. 5(A-B) illustrate that $CD14^+$ $VNN2^+$ cells are increased in stage IV renal cell carcinoma and prostate cancer patients compared to controls. A) Representative flow diagram from magnetically-enriched $CD14^+$ cells in which $CD14^+$ $VNN2^+$ cells are found in the upper right quadrant in renal cell carcinoma patients (25%) compared to healthy controls (13%). Similarly, $CD14^+$ $HLA-DR^{low/neg}$ cells in this patient were compared to the control. B) Dot plot of $VNN2^+$ expression in $CD14^+$ cells from renal cell carcinoma and prostate cancer patients compared to controls.

SUMMARY

Figure 6:
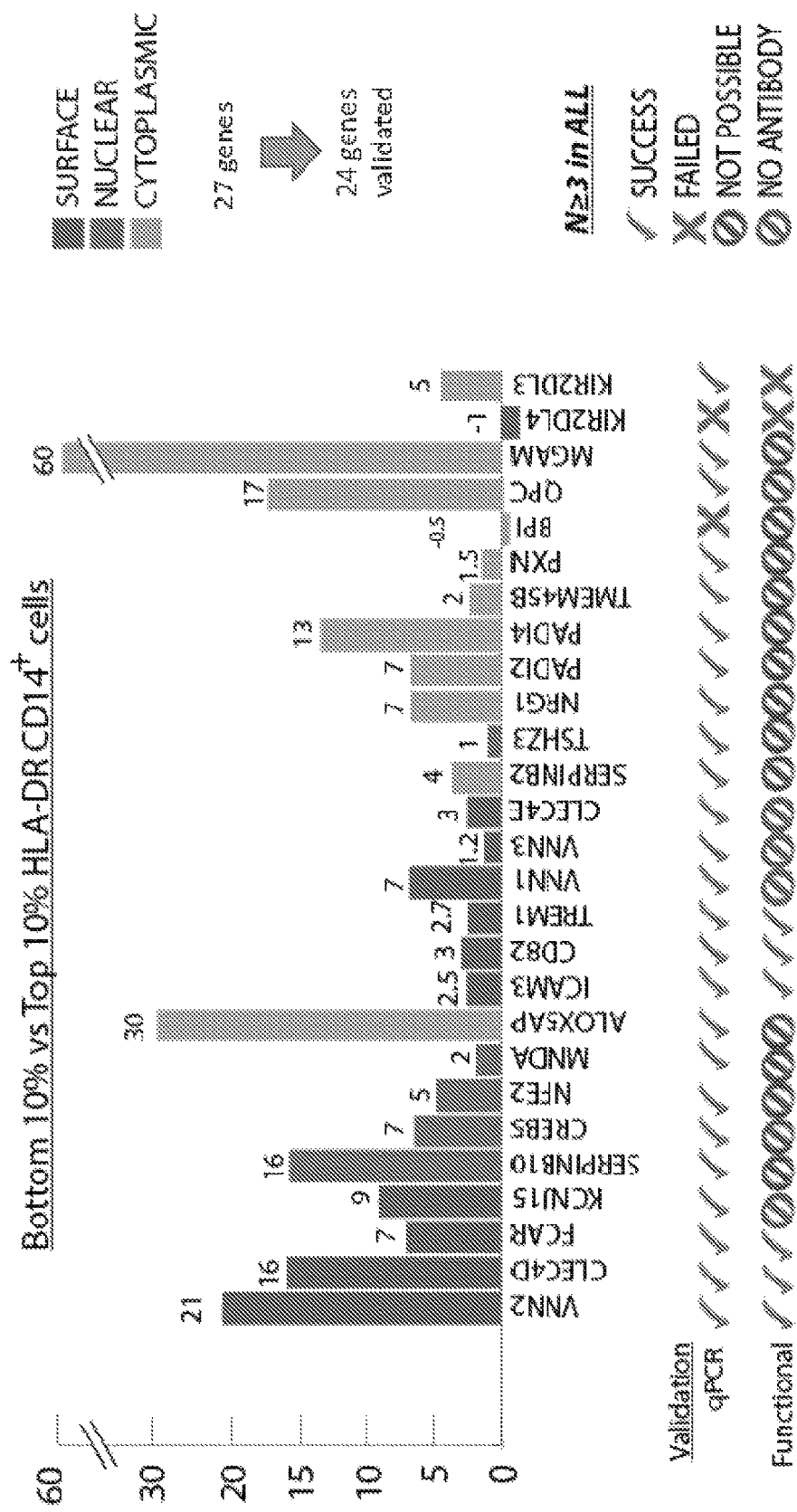
FIG. 6 illustrates a bar graph identifying 27 genes differentially expressed in M-MDSC ($CD14^+$ $HLA-DR^{low}$) compared to $CD14^+$ $HLA-DR^{high}$ monocytes. Also shown is a summary of the results of qPCR and functional live selection assays validating the upregulation of 24 unique genes elevated in M-MDSCs (compared to CD14+ $HLA-DR^{high}$ monocytes).

Embodiments described herein relate to the characterization of an immunosuppressive population of monocytic myeloid derived suppressor cells (M-MDSCs) to identify, quantify and isolate M-MDSCs in a subject.

In some embodiments, the characterization of the immunosuppressive population of monocytic myeloid derived suppressor cells (M-MDSCs) can be used in a method of diagnosing an increased risk of cancer in a subject. The method can include obtaining a blood sample from the subject and determining, in the blood sample, a level of two or more of the inventive markers of polypeptides selected from the group consisting of VNN2, KCNJ15, SERPINB2, CREB5, ICAM3, NFE2, MNDA, PXN, CD89 (FCAR), TSHZ3, NRG1, ALOX5AP, PAD14, PAD12, QPC, VNN1, SERPINB10, CLEC4D, TREM1, CLEC4E, CD82, MGAM, TMEM45B and VNN3. An increase in the level of two or more of the polypeptides compared to a control level is indicative of an increased risk of cancer in the subject.

Other embodiments relate to a method of providing a cancer prognosis in a subject. The method includes obtaining a blood sample from the subject and determining, in the blood sample, a level of two or more of the inventive markers polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3. An increase in the level of two or more of the polypeptides compared to a control level indicates a poor prognosis.

Other embodiments relate to a method of determining the efficacy of a cancer therapeutic, which affects M-MDSC mediated immunosuppression in treating a cancer. The method includes administering a therapeutic agent to an animal. The method further includes obtaining a blood sample from the animal and determining, in the blood sample, a level of two or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3. A decrease in the level of two or more of the polypeptides compared to a control level indicates an effective cancer therapeutic.

Still other embodiments relate to a method of determining the risk of an autoimmune disease in a subject. The method includes obtaining a blood sample from the subject and determining a level of two or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3. A decrease in two or more of the polypeptide biomarkers is indicative of an increased risk of an autoimmune disease in the subject.

Yet other embodiments relate to a method of treating a cancer in a subject. The method includes administering to the subject a therapeutically effective amount of an agent that decreases the expression of one or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3. A decrease in the expression of one or more of the polypeptides decreases M-MDSC immunosuppression in the subject.

DETAILED DESCRIPTION

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

As used herein, the term "subject" and "individual" are used herein interchangeably. They refer to a human or another mammal (e.g., primate, dog, cat, goat, horse, pig, mouse, rat, rabbit, and the like), that can be afflicted with cancer, such as renal, prostate or glioblastoma cancer but may or may not have the disease. In many embodiments, the subject is a human being.

As used herein, the term "diagnosis" and "diagnosing" refers to a process aimed at determining if an individual is afflicted with a disease or ailment. "Diagnosis" can also encompass diagnosis in the context of rational therapy, in which the diagnosis guides therapy, including initial selection of therapy, modification of therapy (e.g., adjustment of dose and/or dosage regimen), and the like. Diagnosis does not imply certainty with regard to the nature of the disease or condition identified, but rather the substantial likelihood that the disease or condition is present. For example, a subject diagnosed as having renal cancer may be 10× or 100× more likely to have renal cancer relative to a subject that has not been diagnosed as having renal cancer. In the context of the present invention, "diagnosing cancer" refers to a process aimed at one or more of: determining if a subject is likely to develop cancer; determining if a subject is afflicted with cancer; determining if a subject is afflicted with a particular stage of cancer; and/or determining if a subject is afflicted with a metastatic cancer.

As used herein, the term "prognosis" refers to a prediction of the probable course and outcome of a disease, or the likelihood of recovery from a disease. Prognosis is distinguished from diagnosis in that it is generally already known that the subject has the disease, although prognosis and diagnosis can be carried out simultaneously. In the case of a prognosis for cancer, the prognosis may be categorized by the relative severity of the cancer according to current standards in clinical staging. "Cancer staging" as used herein, is the process of determining how much cancer is in the body and where it is located. Staging describes the severity of an individual's cancer based on the magnitude of the original (primary) tumor as well as on the extent cancer has spread in the body.

As used herein, the term "biological sample" is used in its broadest sense. A biological sample may be obtained from a subject (e.g., a human) or from components (e.g., tissues) of a subject. The sample may be of any biological tissue or fluid with which biomarkers of the present invention may be assayed. Frequently, the sample will be a "clinical sample", i.e., a sample derived from a patient. Such samples include, but are not limited to, bodily fluids, e.g., urine, whole blood, blood plasma, saliva; tissue or fine needle biopsy samples; and archival samples with known diagnosis, treatment and/or outcome history. The term biological sample also encompasses any material derived by processing the biological sample. Derived materials include, but are not limited to, cells (or their progeny) isolated from the sample, proteins or nucleic acid molecules extracted from the sample. Processing of the biological sample may involve one or more of, filtration, distillation, extraction, concentration, inactivation of interfering components, addition of reagents, and the like. In some embodiments, the biological sample is a whole blood sample. In some embodiments, the biological sample includes peripheral blood mononuclear cells (PBMCs) obtained from a subject. PBMCs can be extracted from whole blood using ficoll, a hydrophilic polysaccharide that separates layers of blood, and gradient centrifugation, which will separate the blood into a top layer of plasma, followed by a layer of PBMCs and a bottom fraction of polymorphonuclear cells (such as neutrophils and eosinophils) and erythrocytes.

As used herein, the terms "normal" and "healthy" are used herein interchangeably. They refer to an individual or group of individuals who have not shown any cancer symptoms and have not been diagnosed with cancer. Preferably, said normal individual (or group of individuals) is not on medication affecting cancer cell growth. In certain embodiments, normal individuals have similar sex, age, body mass index as compared with the individual from which the sample to be tested was obtained. The term "normal" is also used herein to qualify a sample isolated from a healthy individual.

As used herein, the term "control sample" refers to one or more biological samples isolated from an individual or group of individuals that are normal (i.e., healthy). The term "control sample" (or "control") can also refer to the compilation of data derived from samples of one or more individuals classified as normal, or one or more individuals diagnosed with a particular cancer. The control value can take a variety of forms. The control value can be a single cut-off value, such as a median or mean. Control values for the level of an inventive cancer biomarker expression in biological samples obtained, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference.

As used herein, the term "biomarker" refers to a protein selected from the set of proteins provided by the present invention and whose expression profile was found to be indicative of cancer, such as renal, prostate, or glioblastoma cancer. The term "biomarker" also encompasses nucleic acid molecules comprising a nucleotide sequence, which codes for a marker protein of the present invention as well as polynucleotides that hybridize with portions of these nucleic acid molecules.

As used herein, the term "indicative of cancer", when applied to a biomarker, refers to an expression pattern or profile, which is diagnostic of cancer such that the expression pattern is found significantly more often in subjects with the disease than in patients without the disease or another subtype of the disease such as non-metastatic cancer (as determined using routine statistical methods setting confidence levels at a minimum of 95%). Preferably, an expression pattern, which is indicative of cancer is found in at least 60% of patients who have the disease and is found in less than 10% of subjects who do not have the disease. More preferably, an expression pattern which is indicative of cancer is found in at least 70%, at least 75%, at least 80%, at least 85%, at least 90%, at least 95% or more in patients who have the disease and is found in less than 10%, less than 8%, less than 5%, less than 2.5%, or less than 1% of subjects who do not have the disease.

As used herein, the term "differentially expressed biomarker" refers to a biomarker whose abundance level is different in a subject (or a population of subjects) afflicted with cancer or stage of cancer relative to its level in a healthy or normal subject (or a population of healthy or normal subjects). Differential expression includes quantitative, as well as qualitative, differences in the temporal or cellular expression pattern of the biomarker. As described in greater details below, a differentially expressed biomarker, alone or in combination with other differentially expressed biomarkers, is useful in a variety of different applications in diagnostic, sub-typing, therapeutic, drug development and related areas. The expression patterns of the differentially expressed biomarkers disclosed herein can be described as a fingerprint or a signature of cancer, cancer subtype and cancer progression. They can be used as a point of reference to compare and characterize unknown samples and samples for which further information is sought. The term "decreased level" as used herein, refers to a decrease in the abundance level of one or more of the biomarkers described herein of at least 10% or more. For example, 20%, 30%, 40%, or 50%, 60%, 70%, 80%, 90% or more, or a decrease of greater than 1-fold, 2-fold, 3-fold, 4-fold, 5-fold, 10-fold, 50-fold, 100-fold or more as measured by one or more methods described herein. The term "increased level" as used herein, refers to an increase in the abundance one or more of the biomarkers described herein of at least 10% or more. For example, 20%, 30%, 40%, or 50%, 60%, 70%, 80%, 90% or more, or an increase of greater than 1-fold, 2-fold, 3-fold, 4-fold, 5-fold, 10-fold, 50-fold, 100-fold or more as measured by one or more methods, such as method described herein.

As used herein, the terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

As used herein, the term "protein analog", as used herein, refers to a polypeptide that possesses a similar or identical function as the full-length native protein but need not necessarily comprise an amino acid sequence that is similar or identical to the amino acid sequence of the protein, or possesses a structure that is similar or identical to that of the protein. Preferably, in the context of the present invention, a protein analog has an amino acid sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the full-length native protein.

As used herein, the term "protein fragment", as used herein, refers to a polypeptide comprising an amino acid sequence of at least 4 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

As used herein, the terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products.

As used herein, the term "a reagent that specifically detects levels" refers to one or more reagents used to detect the level of one or more biomarkers (e.g., a polypeptide selected from the marker proteins provided herein, a nucleic acid molecule comprising a polynucleotide sequence coding for a marker protein, or a polynucleotide that hybridizes with at least a portion of the nucleic acid molecule). Examples of suitable reagents include, but are not limited to, antibodies capable of specifically binding to a marker protein of interest, nucleic acid probes capable of specifically hybridizing to a polynucleotide sequence of interest, or PCR primers capable of specifically amplifying a polynucleotide sequence of interest. The term "amplify" is used herein in the broad sense to mean creating/generating an amplification product. "Amplification", as used herein, generally refers to the process of producing multiple copies of a desired sequence, particularly those of a sample. A "copy" does not necessarily mean perfect sequence complementarity or identity to the template sequence.

As used herein, the term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

As used herein, the terms "array", "micro-array", and "biochip" are used herein interchangeably. They refer to an arrangement, on a substrate surface, of hybridizable array elements, preferably, multiple nucleic acid molecules of known sequences. Each nucleic acid molecule is immobilized to a discrete spot (i.e., a defined location or assigned position) on the substrate surface. The term "micro-array" more specifically refers to an array that is miniaturized so as to require microscopic examination for visual evaluation.

As used herein, the term "probe", as used herein, refers to a nucleic acid molecule of known sequence, which can be a short DNA sequence (i.e., an oligonucleotide), a PCR product, or mRNA isolate. Probes are specific DNA sequences to which nucleic acid fragments from a test sample are hybridized. Probes specifically bind to nucleic acids of complementary or substantially complementary sequence through one or more types of chemical bonds, usually through hydrogen bond formation.

As used herein, the terms "labeled", "labeled with a detectable agent" and "labeled with a detectable moiety" are used herein interchangeably. These terms are used to specify that an entity (e.g., a probe) can be visualized, for example, following binding to another entity (e.g., a polynucleotide or polypeptide). Preferably, the detectable agent or moiety is selected such that it generates a signal which can be measured and whose intensity is related to the amount of bound entity. In array-based methods, the detectable agent or moiety is also preferably selected such that it generates a localized signal, thereby allowing spatial resolution of the signal from each spot on the array. Methods for labeling polypeptides or polynucleotides are well-known in the art. Labeled polypeptides or polynucleotides can be prepared by incorporation of or conjugation to a label, that is directly or indirectly detectable by spectroscopic, photochemical, biochemical, immunochemical, electrical, optical, or chemical means. Suitable detectable agents include, but are not limited to, various ligands, radionuclides, fluorescent dyes, chemiluminescent agents, microparticles, enzymes, calorimetric labels, magnetic labels, and haptens. Detectable moieties can also be biological molecules such as molecular beacons and aptamer beacons.

As used herein, the term "cancer expression profile map" refers to a presentation of expression levels of a set of biomarkers in a particular status of cancer (e.g., absence of disease, cancer, early stage cancer, metastatic cancer). The map may be presented as a graphical representation (e.g., on paper or a computer screen), a physical representation (e.g., a gel or array) or a digital representation stored in a computer-readable medium. Each map corresponds to a particular status of the disease, and thus provides a template for comparison to a patient sample. In certain preferred embodiments, maps are generated from a plurality of samples obtained from a significant number of normal individuals or individuals with the same status of cancer. Maps may be established for individuals with matched age, sex and body mass index.

Human Myeloid-Derived Suppressor Cells (MDSCs) are a class of cells found to be increased in the blood of patients with cancer in virtually all human cancers tested. The increase in numbers of circulating monocytic MDSCs (M-MDCSs) is generally regarded as indicative of a poor prognosis even with therapy since M-MDSCs block the body's ability to fight cancer cells.

Embodiments described herein relate to the characterization of an immunosuppressive population of monocytic myeloid derived suppressor cells (M-MDSCs) using surface markers specific for M-MDSC. The positive surface markers can be used to identify, quantify and isolate M-MDSCs in a subject. For example, using an RNA array comparison between flow cytometry purified common monocytes (CD14$^+$ HLA-DR$^{high}$) vs M-MDSC (CD14$^+$ HLA-DR$^{negative}$) and qPCR validation, 24 unique genes (Table 1) were identified that are elevated in M-MDSC compared to CD14$^+$ HLA-DR$^{high}$ monocytes. Functional assays demonstrated that M-MDSC cells selected using surface markers identified in the RNA array show suppressive capabilities in vitro. Accordingly, a panel of biomarkers can be used to characterize an immunosuppressive population of monocytic myeloid derived suppressor cells (M-MDSCs) wherein the level of two or more of the polypeptides compared to control levels of the biomarkers in a blood sample obtained from a subject provides a prognostic correlation with an increased risk of cancer and/or stage of cancer in a subject.

The markers described herein listed in Table 1 can be used in the present methods as prognostic tools to more accurately diagnose a subject's cancer and determine if a subject has an increased risk of cancer and/or a particular stage of cancer. The upregulation of these markers reflect an early increase in the circulating levels of M-MDSCs in the peripheral blood of a subject that indicates an increased risk of cancer as well as an increased risk of metastatic cancer in a subject. The indicated markers can be used as prognostic indicators to trigger standard and effective therapeutic interventions, in some cases earlier than currently prescribed, likely lowering the risk of terminal cancer.

M-MDSCs whose abundance changes in blood due to cancer, express surface proteins, which can discriminate subjects having cancer from healthy controls. Therefore, in some embodiment, a method for diagnosing a cancer or an increased risk of a cancer in a subject can include obtaining a blood sample from subject. A level of two or more of the polypeptides selected from the group consisting of VNN2, KCNJ15, SERPINB2, CREB5, ICAM3, NFE2, MNDA, PXN, CD89 (FCAR), TSHZ3, NRG1, ALOX5AP, PAD14, PAD12, QPC, VNN1, SERPINB10, CLEC4D, TREM1, CLEC4E, CD82, MGAM, TMEM45B and VNN3 (shown in Table 1) can then be determined. The increase in level of two or more of these polypeptide cancer biomarkers when compared to a control level is indicative of a cancer or an increased risk of cancer in a subject.

In some embodiments, the method includes determining a level of 3, 4, 5, 6, 7, 8, 9, or 10 of the polypeptide cancer biomarkers described herein. In some embodiments, the method includes determining a level of 4, 5, or 6, of the polypeptide cancer biomarkers described herein. In certain embodiments, the method includes determining a level of VNN2, CLEC4D, FCAR, KCNJ15, SERPINB10, and CREB5. In an exemplary embodiment shown in FIG. 2, the method includes determining a level of VNN2, CLEC4D, CD82, ICAM3, KCNJ15, and TREM1.

Other M-MDSC cancer biomarkers contemplated by the herein include nucleic acid molecules including polynucleotide sequences coding for the inventive protein markers described in Table 1 (or analogs and fragments thereof) and polynucleotides that hybridize with portions of these nucleic acid molecules.

TABLE 1

| VNN2 | FCAR | SERPINB10 |
| KCNJ15 | TSHZ3 | CLEC4D |
| SERPINB2 | NRG1 | TREM1 |
| CREB5 | ALOX5AP | CLEC4E |
| ICAM3 | PADI4 | CD82 |
| NFE2 | PAD12 | MGAM |
| MNDA | QPC | TMEM45B |

In certain embodiments, determining the presence or absence of additional cell lineage biomarkers can be included in a cancer assay described herein. For example, in addition to determining the levels of two or more of the polypeptides of Table 1, the expression level of lineage markers (LIN), CD14 and/or HLA-DR may determined in order to further identify a M-MSDC populations in a subject.

Information on levels of a given set of biomarkers obtained using biological samples from individuals afflicted with cancer may be grouped to form a cancer expression profile map. In some embodiments, a cancer expression profile map can result from the study of a large number of individuals with the same disease sub-type. In certain embodiments, a cancer expression profile map can be established using samples from individuals with matched age, sex, and body index. The expression profile map can provide a template for comparison to biomarker expression patterns generated from unknown biological samples. Cancer expression profile maps may be presented as a graphical representation (e.g., on paper or a computer screen), a physical representation (e.g., a gel or array) or a digital representation stored in a computer-readable medium.

As will be appreciated by those of ordinary skill in the art, sets of biomarkers whose expression profiles correlate with cancer may be used to identify, study, or characterize unknown biological samples, e.g., blood samples obtained from a subject. Accordingly, in one aspect, methods for characterizing biological samples obtained from a subject suspected of having cancer, for diagnosing cancer in a subject, and for assessing the responsiveness of cancer in a subject to treatment are contemplated. In such methods, the biomarkers' expression levels determined for a biological sample obtained from the subject, are compared to the levels in one or more control samples. The control samples may be obtained from a healthy individual (or a group of healthy individuals), and/or from an individual (or group of individuals) afflicted with cancer. The control expression levels of the biomarkers of interest are preferably determined from a significant number of individuals, and an average or mean is obtained. In certain aspects of the invention, the levels determined for the biological sample under investigation are compared to at least one expression profile map for cancer, as described above.

The methods described herein can be applied to the study of any type of biological samples allowing one or more inventive biomarkers to be assayed. Examples of biological samples for use in a method include, but are not limited to, blood and blood products (e.g., blood plasma). In a particular aspect, the biological sample is whole blood or PBMCs obtained from the subject using well known methods. In an exemplary embodiment, CD14+ common monocyte cells can be positively selected from a subject's blood sample (e.g., PBMC) prior to further characterization using magnetic CD14+ microbeads with a magnet. CD14+ cells can then be flow-sorted into M-MDSCs using flow cytometry.

The biological samples used in the methods may be fresh or frozen samples collected from a subject, or archival samples with known diagnosis, treatment and/or outcome history. Samples can be stored for varying amounts of time, such as being stored for an hour, a day, a week, a month, or more than a month. Biological samples may be collected by any means. In some embodiments, blood samples are obtained via intravenous (i.v.) blood draw. In certain aspects, the inventive methods are performed on the biological sample itself without or with limited processing of the sample.

Preferably, there is enough of the biological sample to accurately and reliably determine the abundance of the set of biomarkers of interest. Multiple biological samples may be taken from the subject in order to obtain a representative sampling from the subject.

In still other embodiments, the inventive methods can be performed on a protein extract prepared from the biological sample. The protein extract can contain the total protein content. However, the methods may also be performed on extracts containing one or more of: membrane proteins, nuclear proteins, and cytosolic proteins. Methods of protein extraction are well known in the art (see, for example "Protein Methods", D. M. Bollag et al., 2nd Ed., 1996, Wiley-Liss; "Protein Purification Methods: A Practical ApprIPSch", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.).

Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User guides that describe in great detail the protocol to be followed are usually included in all these kits. Sensitivity, processing time and costs may be different from one kit to another. One of ordinary skill in the art can easily select the kits most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

In yet other aspects, the methods can be performed on nucleic acid molecules extracted from the biological sample. For example, RNA may be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

In certain aspects, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNApolymerases (such as avian myeloblastosis virus reverse transcriptase or Moloney murine leukemia virus reverse transcriptase).

The diagnostic methods can involve the determination of the abundance levels of a plurality (i.e., two or more, e.g., at least 3, at least 4, at least 5, at least 6, at least 7, at least 8, at least 9, at least 10 or more) of polypeptides in a biological sample obtained from a subject. Determination of protein levels can be performed by any suitable method (see, for example, E. Harlow and A. Lane, "Antibodies: A Laboratories Manual", 1988, Cold Spring Harbor Laboratory: Cold Spring Harbor, N.Y.).

In general, protein levels are determined by contacting a biological sample obtained from a subject with binding agents for two or more of the protein markers listed in Table 1, determining, in the sample, the levels of polypeptides that bind to the binding agents; and comparing the levels of polypeptides in the sample with the levels of polypeptides in a control sample. As used herein, the term "binding agent" refers to an entity such as a polypeptide or antibody that specifically binds to an inventive protein marker. An entity "specifically binds" to a polypeptide if it reacts/interacts at a detectable level with the polypeptide but does not react/interact detectably with peptides containing unrelated sequences or sequences of different polypeptides.

In certain aspects, the binding agent is a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

In other aspects, the binding agent is an antibody specific for a protein marker. Examples of antibodies for use in the methods include monoclonal and polyclonal antibodies, immunologically active fragments (e.g., Fab or (Fab)2 fragments), antibody heavy chains, humanized antibodies, antibody light chains, and chimeric antibodies. Antibodies, including monoclonal and polyclonal antibodies, fragments and chimeras, may be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czemik et al., NeuroNeuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof is bound. The bound antibodies can then be eluted from the column using a buffer with a high salt concentration. Instead of being prepared, antibodies to be used in the methods of the present invention may be obtained from scientific or commercial sources.

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or analog or fragment thereof). The detectable agent can be selected such that it generates a signal which can be measured and whose intensity is related (preferably proportional) to the amount of protein marker present in the sample being analyzed. Methods for labeling biological molecules such as polypeptides and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain aspects, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein levels in the diagnostic methods of the present invention may be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay may be competitive or noncompetitive. Methods of detection and quantification of the signal generated by the complex formed by binding of the binding agent with the protein marker will depend on the nature of the assay and of the detectable moiety (e.g., fluorescent moiety).

In some embodiments, image flow cytometry can be employed for determining a level of 2 or more of the polypeptide cancer biomarkers described herein. In standard flow cytometry, specific cell populations in a blood sample, drawn from a subject and fluorescently labeled, are passed in single file through a flow stream to be interrogated by a light source (usually a laser). Fluorescence and light scattering signals emitted, or remitted, by the cells in response to the light source can be employed to determine the types and the number of the cells. In certain embodiments, a flow cytometry assay for use in a method described herein can include a specific multicolor flow cytometry antibody panel able to rapidly identify and quantify M-MDSCs in a sample obtained from a subject with a very high level of sensitivity through assessment of the expression of two or more inventive cancer biomarkers.

Exemplary flow cytometry panels for use in a method described herein can include Panels 1-3 below where each biomarker is conjugated with a different fluorescent label. A wide range of fluorophores can be used as labels in flow cytometry. Fluorophores are typically attached to an antibody that recognizes an inventive polypeptide surface biomarker. Each fluorophore has a characteristic peak excitation and emission wavelength, and the emission spectra often overlap. Consequently, the combination of labels which can be used depends on the wavelength of the lamp(s) or laser(s) used to excite the fluorochromes and on the detectors available.

PANEL 1) LIN-FITC, CD14-PERCPCY5.5, HLA DR-APC-CY7, CD89-PE, MNDA-APC
PANEL 2) LIN-FITC, CD14-PERCPCY5.5, HLA DR-APC-CY7, VNN2-PE, CLEC4d-APC, ICAM3 (CD50)
PANEL 3) LIN-FITC, CD14-PERCPCY5.5, HLA DR-APC-CY7, CD82-Alexa 647, TREM1-PE Alternatively, the protein levels may be determined using mass spectrometry based methods or image (including use of labeled ligand) based methods known in the art for the detection of proteins. Other suitable methods include proteomics-based methods. Proteomics, which studies the global changes of protein expression in a sample, typically includes the following steps: (1) separation of individual proteins in a sample by electrophoresis (I-D PAGE), (2) identification of individual proteins recovered from the gel (e.g., by mass spectrometry or N-terminal sequencing), and (3) analysis of the data using bioinformatics.

In certain aspects, the assay will be an immunohistochemisty assay employing antibodies specific for the inventive cancer biomarkers, although gene screening assays in which the level of expression of the DNA encoding these biomarkers or detecting the level of mRNA transcribed for these markers also will be useful in this context. Detection of these markers may be performed on single samples, for example on a single slide, or on multiple samples, for example on separate slides. Thus, both gene and protein detection of biomarkers on a single tissue sample is envisioned.

In some embodiments, the level of expression of a cancer biomarker can be determined by measuring the level of a protein. While an immunoassay can be used, the level of biomarker expression can also be determined by purifying the expressed protein and directly determining its level of expression. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified and/or quantified using chromatographic and electrophoretic techniques to achieve partial or complete purification (or purification to homogeneity). Analytical methods particularly suited to the preparation of a pure peptide are immunohistochemistry, ion-exchange chromatography, exclusion chromatography; polyacrylamide gel electrophoresis; isoelectric focusing. A particularly efficient method of purifying peptides is fast protein liquid chromatography or even HPLC.

As discussed above, the diagnostic methods may involve determination of the expression levels of a set of nucleic acid molecules comprising polynucleotide sequences coding for an inventive protein marker. Determination of expression levels of nucleic acid molecules in the practice of the methods may be performed by any suitable method, including, but not limited to, Southern analysis, Northern analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

In some embodiments, the level of expression of an inventive cancer biomarker gene can be obtained by determining the relative levels of mRNA being expressed, using, for example, quantitative real-time polymerase chain reaction (qPCR). A key feature of qPCR is that the amplified DNA is detected as the reaction progresses in real time. This differs from standard PCR, where the product of the reaction is detected at its end. Two common methods for detection of products in real-time PCR are non-specific fluorescent dyes that intercalate with any double-stranded DNA, and sequence-specific DNA probes consisting of oligonucleotides that are labeled with a fluorescent reporter which permits detection only after hybridization of the probe with its complementary DNA target. See VanGuilder et al., Biotechniques 44 (5): 619-626 (2008).

In an exemplary embodiment using qPCR, 5 ml of whole blood from renal cancer patient or healthy control is incubated with 10 ml of cell lysis buffer ACK 5 minutes. Blood is spun at 1500 rpm, pellet resuspended in 10 ml ACK cell lysis buffer and further incubated 5 minutes. Sample is spun and RNA is extracted using Qiagen RNA extraction kit. RNA is then reverse-transcribed into cDNA and quanitative PCR applied using specific primers for VNN2, CLEC4D, FCAR, KCNJ15, SERPINB10 and CREB5. Values obtained from renal cancer blood qPCR are compared to values obtained from normal blood qPCR as show in FIG. 7.

As used herein, the terms "expression levels" of an inventive cancer biomarker refers to the amount of a protein that is present or the amount of mRNA transcribed from the gene coding for an inventive protein marker that is present. The expression level can be detected with or without comparison to a level from a control sample or a level expected of a control sample. The expression level can be determined by measuring the amount of mRNA, or by measuring the amount of protein formed from the mRNA. In some embodiments, the expression level of the an inventive cancer biomarker gene may be increased by at least about 2 fold, at least about 5 fold, at least about 10 fold, at least about 20 fold, or at least about 50 fold. In some aspects of the invention, the level of an inventive cancer biomarker is considered increased if an assay indicates that a particular measurement, amount or level is at about or at least about 80%, 75%, 70%, 65%, 60%, 55%, 50%, 45%, 40%, 35%, 30%, 25%, 20%, 15%, 10%, 5% or greater than the measurement, amount or level observed in subjects or samples that have normal levels of a given cancer biomarker. Alternatively, in some aspects of the invention, the expression level of an inventive cancer biomarker is considered increased if an assay indicates that a particular measurement, amount or level is about or at least about 1, 2, 3, 4, 5, 6, 7, 8, 9, 10 or more standard deviations above the measurement, amount or level observed in subjects that have normal levels of an inventive cancer biomarker. In other cases, expression levels may be considered increased if a measurement, amount or level indicative of an inventive cancer biomarker is or is at most 2, 3, 4, 5, 6, 7, 8, 9, 10, 15, 20, 25, 30, 35, 40, 45, 50 or more times more than the measurement, amount, or level indicative of an inventive cancer biomarker in normal subjects.

Nucleic acid probes for use in the detection of polynucleotide sequences in biological samples may be constructed using conventional methods known in the art. Suitable probes may be based on nucleic acid sequences encoding at least 5 sequential amino acids from regions of nucleic acids encoding a protein marker, and preferably comprise about 15 to about 50 nucleotides. A nucleic acid probe may be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well-known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes may be used in hybridization techniques to detect polynucleotides encoding the protein markers. The technique generally involves contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for a protein marker may involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a protein marker.

Hybridization and amplification techniques described herein may be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker may be used as targets in a microarray. A number of different array configurations and methods of their production are known to those skilled in the art (see, for example, U.S. Pat. Nos. 5,445,934; 5,532,128; 5,556,752; 5,242,974; 5,384, 261; 5,405,783; 5,412,087; 5,424,186; 5,429,807; 5,436, 327; 5,472,672; 5,527,681; 5,529,756; 5,545,531; 5,554, 501; 5,561,071; 5,571,639; 5,593,839; 5,599,695; 5,624, 711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., *Proc. Natl. Acad. Sci. USA* 1996, 93: 10614-10619; Chen et al., *Genomics,* 1998, 51: 313324; U.S. Pat. Nos. 5,143,854; 5,445,934; 5,807,522; 5,837, 832; 6,040,138; 6,045,996; 6,284,460; and 6,607,885).

Once the levels of the biomarkers of interest have been determined for the biological sample being analyzed, they are compared to the levels in one or more control samples or to at least one expression profile map for cancer described herein. Comparison of levels according to methods of the present invention is preferably performed after the levels obtained have been corrected for both differences in the amount of sample assayed and variability in the quality of the sample used (e.g., amount of protein extracted, or amount and quality of mRNA tested). Correction may be carried out using different methods well-known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

For a given set of biomarkers, comparison of an expression pattern obtained for a biological sample against an expression profile map established for cancer or a particular subtype of cancer may comprise comparison of the normalized levels on a biomarker-by-biomarker basis and/or comparison of ratios of levels within the set of biomarkers. In addition, the protein expression pattern obtained for the biological sample being analyzed, may be compared against each of the expression profile maps (e.g., expression profile map for non-cancer, expression profile map for cancer, expression profile map for metastatic cancer, expression profile map for an early stage cancer) or against an expression profile that defines delineations made based upon all the cancer expression profile maps.

Cancers diagnosed in a method described herein can include, but are not limited to, breast cancer, melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

In some embodiments the cancer diagnosed is a solid tumor. Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). For example, the solid tumor can include a renal cell carcinoma, prostate cancer, glioblastoma, ovarian cancer, breast cancer, colon cancer (adenocarcinoma) or malignant melanoma. In particular embodiments, the cancer is a carcinoma solid tumor, e.g., a stage IV renal carcinoma. In some embodiments, cancer diagnosed in a method described herein can include metastatic cancer.

Using methods described herein, skilled physicians may select and prescribe treatments adapted to each individual subject based on the diagnosis of a cancer or stage of cancer provided to the subject through determination of the levels of the inventive biomarkers. In particular, the present invention provides physicians with a non-subjective means to diagnose cancer, which will allow for early treatment, when intervention is likely to have its greatest effect. Selection of an appropriate therapeutic regimen for a given patient may be made based solely on the diagnosis provided by the inventive methods. Alternatively, the physician may also consider other clinical or pathological parameters used in existing methods to diagnose cancer and assess its advancement.

In another aspect, the present invention provides kits comprising materials useful for carrying out diagnostic methods according to the present invention. The diagnosis and sub-typing procedures described herein may be performed by diagnostic laboratories, experimental laboratories, or practitioners. The invention provides kits, which can be used in these different settings.

Materials and reagents for characterizing biological samples, diagnosing cancer, and/or sub-typing cancer in a subject according to the inventive methods may be assembled together in a kit. In certain aspects, an inventive kit comprises at least one reagent that specifically detects levels of one or more inventive biomarkers, and instructions for using the kit according to a method of the invention. Each kit may preferably include the reagent, which renders the procedure specific. Thus, for detecting/quantifying a protein marker (or an analog or fragment thereof), the reagent that specifically detects levels of the protein may be an antibody that specifically binds to the protein marker (or analog or fragment thereof). For detecting/quantifying a nucleic acid molecule comprising a polynucleotide sequence coding a protein marker, the reagent that specifically detects expression levels may be a nucleic acid probe complementary to the polynucleotide sequence (e.g., cDNA or an oligonucleotide). The nucleic acid probe may or may not be immobilized on a substrate surface (e.g., beads, a microarray, and the like).

Depending on the procedure, the kit may further comprise one or more of, extraction buffer and/or reagents, amplification buffer and/or reagents, hybridization buffer and/or reagents, immunodetection buffer and/or reagents, labeling buffer and/or reagents, and detection means. Protocols for using these buffers and reagents for performing different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain aspects, the kits of the present invention further include control samples. In other aspects of the invention, the inventive kits include at least one expression profile map for cancer and/or cancer sub-type as described herein for use as comparison template. Preferably, the expression profile map is digital information stored in a computer-readable medium.

Instructions for using the kit, according to one or more methods of the invention, may comprise instructions for processing the biological sample obtained from the subject, and/or for performing the test, instructions for interpreting the results. As well as a notice in the form prescribed by a governmental agency (e.g., FDA) regulating the manufacture, use or sale of pharmaceuticals or biological products.

Further embodiments include providing a therapeutic intervention for a subject identified as having a substantially increased risk of having cancer. The therapeutic intervention can be provided as a follow-up step to a diagnosis of a subject having cancer as a result of carrying out any of the methods of diagnosis described herein. Examples of types of treatment for cancer are surgery, radiation therapy (e.g., internal radiation therapy using strontium-89, proton beam radiation therapy) hormone therapy, chemotherapy, biologic therapy, targeted therapy (e.g., monoclonal antibody therapy), and high-intensity focused ultrasound.

Several of the therapeutic interventions described above can be characterized as treatment with an anticancer agent. These include forms of hormone therapy, chemotherapy, and biologic therapy. Examples of anticancer agents useful for hormone therapy include luteinizing hormone-releasing hormone agonists, antiandrogens, ketoconazole, aminoglutethimide, and estrogens. Examples of chemotherapeutic and biologic agents include Cabazitaxel, Degarelix, Taxotere (Docetaxel), Enzalutamide, Jevtana (Cabazitaxel), Lupron or Viadur (Leuprolide Acetate), Prednisone, Prolia or Xgeva (Denosumab), Provenge (Sipuleucel-T), Xofigo (Radium 223 Dichloride), Sipuleucel-T, Xtandi (Enzalutamide), and Zytiga (Abiraterone Acetate). It is understood that therapeutic agents include any salts, crystal structures, amorphous structures, hydrates, derivatives, metabolites, stereoisomers, structural isomers, and prodrugs.

In some embodiments, the therapeutic intervention can include administering to the subject a therapeutic agent capable of directly or indirectly modulating one or more of the inventive biomarkers of Table 1 in order to increase, or decrease in the case of auto-immune disorders described below, the immunosuppressive capabilities of M-MDSCs in the subject.

Therefore, another aspect of the invention relates to a method of treating a cancer in a subject. The method includes administering to the subject a therapeutically effective amount of an agent that decreases the expression of one or more of the polypeptides selected from the group listed in Table 1, wherein a decrease in the expression of one or more of the polypeptides reduces M-MDSC immunosuppression in the subject.

In some embodiments, two, three, four, five, six, seven, eight, nine, ten or more agents targeted to inventive biomarkers of Table 1 can be administered to the subject in order to modulate expression of two, three, four, five, six, seven, eight, nine, ten or more of the inventive biomarkers. In some embodiments, a single agent modulates the expression of a single corresponding biomarker. In other embodiments, a single agent modulates the expression of two or more corresponding biomarkers in a subject.

A therapeutic agent capable of directly or indirectly modulating one or more of the inventive biomarkers of Table 1 of the present invention may be any molecule that effects a reduction in the activity of one or more of the inventive biomarkers. In an exemplary embodiment, the therapeutic agent can include known inhibitors of the biomarkers of Table 1, for example, a known KCNJ15 potassium channel inhibitor, such as Tertiapin-Q.

A therapeutic agent capable of directly or indirectly modulating one or more of the inventive biomarkers of Table 1 of the present invention can include proteins, peptides, DNA molecules (including antisense), DNA fragments, DNA plasmids, RNA molecules (including iRNA agents and antisense) and small molecules. The term "iRNA agent," as used herein, refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

In certain embodiments, a therapeutic agent can include an iRNA agent directed to an inventive biomarker of Table 1. In an exemplary embodiment, a therapeutic agent for use in a method described herein can include a small interfering RNA (siRNA), such as a si/shRNA directed against SERPINB10. Without being bound by theory, it is believed that the inhibition of SERPINB10 can reduce the suppressive nature of M-MDSCs in a subject with cancer, thus allowing for $CD8^+$ T cell targeting of a subject's cancer cells.

Methods of delivering RNAi interfering (RNAi) agents, or vectors containing; nucleic acids, to the target cells (e.g., M-MDSCs) can include, for example directly contacting the cell with a composition comprising a modulatory nucleic acid, or local or systemic injection of a composition containing the nucleic acid. In one embodiment, nucleic acid agents (e.g., RNAi, siRNA), or other nucleic acid, expression vectors that encode agonists (including viral vectors) are injected directly into a tumor or lymph system. In some embodiments agonist nucleic may be delivered by systemic administration, wherein the nucleic acid is complexed with, or alternatively contained within a carrier. Example carriers for modulatory nucleic acid agents include, but are not limited to, peptide carriers, viral vectors, gene therapy reagents, and/or liposome carrier complexes and the like.

Alternatively, the nucleic acid agent may be administered in liposomes or microspheres (or microparticles). Methods for preparing liposomes and microspheres for administration to a patient are well known to those of skill in the art. U.S. Pat. No. 1,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979) also U.S. Pat. Nos. 4,906,474, 4,925,673 and 3,625,214, and Jein, TIPS 19:155-157 (1998), the contents of which are hereby incorporated by reference.

In some embodiments, the agents described herein for treatment of MDSC related disorders such as cancer and auto-immune disorder (see below), may be administered to a subject in combination with additional pharmaceutically active agents. Exemplary pharmaceutically active compounds/agents include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

It is further contemplated that the biomarkers of Table 1 can serve as surrogate markers of therapeutic efficacy for agents targeting various cancers. Since lower levels of the inventive biomarkers are indicative of lower degrees of cancer risk and/or progression, it is contemplated by the present invention that a cancer therapeutic which can lower the level of two or more of the biomarkers of Table 1 in a sample obtained from a subject is an effective cancer therapeutic.

Therefore, in another aspect, a method of determining the efficacy of a cancer therapeutic which affects M-MDSC mediated immunosuppression in treating a cancer is provided. The method includes: (1) administering a therapeutic agent to an animal; (2) obtaining a blood sample from the animal; (3) determining a level of two or more of the inventive biomarkers of Table 1 the sample; and (4) comparing the detected level of two or more of the inventive biomarkers of Table 1 in the sample with a control sample level. According to the present invention, a reduced level of two or more of the inventive biomarkers of Table 1 in the sample compared to the level of two or more of the inventive biomarkers of Table 1 in the control sample is indicative of an effective cancer therapeutic or an effective combination of cancer therapeutics. In certain aspects of the invention, the method includes administering the cancer therapeutic to an animal prior to obtaining a blood sample from the animal.

A "cancer therapeutic", as used herein, is capable of negatively affecting cancer in an animal, for example, by inhibiting M-MDSC immunosuppression of $CD8^+$ T cells, by promoting M-MDSC differentiation, reducing the number of circulating M-MDSCs in a subject, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting invasion, migration, spreading, or progression of cancer, or increasing the lifespan of an animal with cancer. Without being bound by theory, a therapeutic identified by the subject screening methods as having one or more of the desired activities may work via any one of a number of mechanisms.

When administered to an animal, the cancer therapeutic can be administered as a pharmaceutical composition comprising a pharmaceutically acceptable carrier. Pharmaceutically acceptable carriers are well known in the art and include, for example, aqueous solutions such as water or physiologically buffered saline or other solvents or vehicles such as glycols, glycerol, oils or injectable organic esters. A pharmaceutically acceptable carrier can contain physiologically acceptable compounds that act, for example, to stabilize or to increase the absorption of the active therapeutic compound. The physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

A pharmaceutical composition can be administered to a subject by various routes including, for example, oral administration; intramuscular administration; intravenous administration; anal administration; vaginal administration; parenteral administration; nasal administration; intraperitoneal administration; subcutaneous administration and topical administration. This may be achieved by administering a single composition or pharmacological formulation that includes one or more cancer therapeutics, or by administering to the animal one or more compositions or formulations, at the same time.

Anti-cancer agents include biological agents (biotherapy), chemotherapy agents, and radiotherapy agents. Additional agents screened can include nucleic acids, peptides, proteins, antibodies, antisense RNAs, RNAi constructs (including siRNAs), DNA enzymes, ribozymes, morpholino constructs, chemical compounds, and small organic molecules. Agents may be screened individually, in combination, or as a library of agents. Agents to be screened in the methods of the present invention can be produced, for example, by bacteria, yeast or other organisms (e.g., natural products), produced chemically (e.g., small molecules, including peptidomimetics), or produced recombinantly.

In many drug screening programs which test libraries of compounds and natural extracts, high throughput assays are desirable in order to maximize the number of compounds surveyed in a given period of time. Assays of the present invention which are performed in cell-free systems may be developed with purified or semi-purified proteins or with lysates, are often preferred as "primary" screens in that they can be generated to permit rapid development and relatively easy detection of an alteration in a molecular target which is mediated by a test agent. Moreover, the effects of cellular toxicity and/or bioavailability of the test agents can be generally ignored in such a system, the assay instead being focused primarily on the effect of the agent.

A primary screen can be used to identify agents that are more likely to have an effect on cancer progression due to M-MDSC immunosuppression, in vitro and/or in vivo. Such a screen for use in the present invention may include a functional assay measuring CD8 T cell immunosuppression. One or more agents which decreases M-MDSC immunosuppression and/or expression of the inventive biomarkers in comparison to a control level in the absence of the one or more agents, is a candidate agent for use in the subject methods. Similarly, M-MDSCs may be contacted with one or more agents (e.g., individual candidate agents, combinations of two or more agents, a library of nucleic acids, polypeptides, small organic molecules, chemical compounds, etc.) and the ability of the agent to decrease the expression level of the inventive biomarkers can be measured.

The efficacy of the agent can be assessed by generating dose response curves from data obtained using various concentrations of the test agent. Moreover, a control assay can also be performed to provide a baseline for comparison. Such candidates can be further tested for efficacy in tumor growth, progression, or spreading in vivo. For example, the efficacy of the agent can be tested in vivo in any animal cancer models related to M-MDSC immunosuppresion.

In another aspect, the markers described herein listed in Table 1 can be used as prognostic tools to more accurately diagnose a subject's autoimmune disease and determine if a subject has an increased risk of autoimmune disease. The importance of regulatory T lymphocytes (Tregs) in the control of autoimmunity is now well established in a variety of experimental animal models. In addition, there are numerous studies suggesting that Treg deficits may be an underlying cause of human autoimmune diseases. The emergence of Tregs as an essential component of immune homeostasis provides a potential therapeutic opportunity for active immune regulation and long-term tolerance induction. M-MDSC cells are capable of regulating immune response in a subject as M-MDSCs can convert CD4 naïve T-cells into T regulatory (Treg) cells. T regs are functionally impaired in the autoimmune disease pathology and effective suppression of T cells by Treg cells is critical for the prevention of spontaneous autoimmune disease.

Therefore, in another aspect of the invention, the level of M-MDSCs as indicated by the level of two or more inventive biomarkers of Table 1 can also be indicative of autoimmune disease or risk thereof in a subject. For example, while an increase in the number of M-MDSCs (as indicated by the increase of two or more of the inventive biomarkers of Table 1) is generally indicative of poor prognosis for cancer therapy since MDSCs block the body's ability to fight cancer cells, a decrease in M-MDSCs in a subject can be indicative of the subject having auto-immune disease as the subject experiences a concurrent reduction in the immunosuppressing effect of M-MDSCs. Accordingly, in some aspects a method of determining the risk of an auto-immune disease in a subject is provided. The method includes a first step of obtaining a blood sample from the subject. The method also includes a second step of determining a level of two or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3, wherein a decrease in two or more of the polypeptide biomarkers is indicative of the presence of and/or an increased risk of an autoimmune disease in the subject.

The language "autoimmune disease" or "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. The terms "autoantigen" and "self-antigen" are used interchangeably herein. The term "self" as used herein is intended to mean any component of a subject and includes molecules, cells, and organs. Autoantigens may be peptides, nucleic acids, or other biological substances.

For example, the methods of the present invention can be used in determining the risk of or prognosis of autoimmune conditions or related inflammatory diseases. Such diseases can include but are not limited to inflammatory bowel disease (IBD), Crohn's disease, rheumatoid arthritis, uveitis, inflammatory bowel disease, asthma, glomerulonephritis, lung fibrosis, Wegener's granulomatosis; chronic obstructive pulmonary disease (COPD); acute respiratory distress syndrome (ARDS); transfusion-related acute lung injury (TRALI); ischemia/reperfusion acute lung injury; and Goodpasture's disease), granulocytopenia, multiple sclerosis, myasthenia gravis (MG), Huntington's disease (HD), amyotrophic lateral sclerosis (ALS), Guillain Bane syndrome, reperfusion following stroke, degenerative discs, cerebral trauma, Parkinson's disease (PD) and Alzheimer's disease (AD), psoriasis, hypersensitivity reactions of the skin, sepsis, atherosclerosis, ischemia-reperfusion injury, myocardial infarction, restenosis, vasculitis, systemic lupus erythematosus (SLE), and insulin-dependent diabetes.

As described above, biomarkers described herein can be used to determine the efficacy of therapeutic agents. For example, an increase in M-MSDC following administration of a therapeutic autoimmune agent or therapy can be indicative of the autoimmune agent or therapy being effective. Therefore, in another aspect of the present invention, a method of determining the efficacy of an autoimmune therapeutic which affects M-MDSC mediated immunosuppression in treating an autoimmune disease is provided. The method includes: (1) administering a therapeutic agent to an animal; (2) obtaining a blood sample from the animal; (3) determining a level of two or more of the inventive biomarkers of Table 1 the sample; and (4) comparing the detected level of two or more of the inventive biomarkers of Table 1 in the sample with a control sample level. According to the present invention, an increased level of two or more of the inventive biomarkers of Table 1 in the sample compared to the level of two or more of the inventive biomarkers of Table 1 in the control sample is indicative of an effective auto-immune therapeutic or an effective combination of therapeutics. In certain aspects of the invention, the method includes administering the autoimmune therapeutic to an animal prior to obtaining a blood sample from the animal.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The following example is included for purposes of illustration and is not intended to limit the scope of the invention.

Example 1

The Surface Extoenzyme VNN2 Identifies CD14+ HLA-DRlow/neg Human Monocytic Myeloid-Derived Suppressor Cells Myeloid Derived Suppressor Cells (MDSC) represent an intrinsic part of the myeloid-cell lineage that were initially described in cancer patients more than two decades ago. MDSC consist of a heterogeneous population of immature cells that expand during cancer, inflammation and infection. In particular, human MDSC are currently classified into granulocytic $CD33^+$ $CD15^+$ $CD14^{neg}$ $CD11b^+$, $HLA-DR^{neg/low}$ (Go-MDSC) or monocytic $CD33^+$ $CD11b^+$ $CD14^+$ $CD15^{neg}$, $HLA-DR^{neg/low}$ (Mo-MDSC) sub-populations.

Monocytes are produced in the bone marrow, and in healthy individuals they quickly differentiate into mature granulocytes, macrophages or dendritic cells (DC). However, under chronic inflammatory conditions such as in cancer, monocyte differentiation can be blocked and results in an expanded M-MDSC population found in peripheral blood. Several surface proteins have been linked to human M-MDSC, but the only current approach in order to specifically isolate them is based upon the low expression of HLA-DR on CD14$^+$ cells and test if they can functionally suppress proliferation. However, the absence of positive markers specific for human M-MDSC is one of the hurdles to the characterization and in-tissue study of these heterogeneous immunosuppressive cell population.

Vascular non-inflammatory molecule 2 (VNN2 or also known as GPI-80) is a GPI-anchored human ectoenzyme that, together with the two other isoforms VNN1 and VNN3, constitutes the Vanin family of proteins. Although VNN2 was initially identified in neutrophils playing a role in their transendothelial migration, it has also been shown to be expressed in a subset of CD14$^+$ monocytes.

Interestingly, Vanins possess pantetheinase activity, being involved in pro-inflammatory and oxidative processes. Although VNN2 was previously characterized to be expressed in a subset of CD14$^+$ monocytes with reduced antigen presentation, superior phagocytosis, high Reactive Oxygen Species production (ROS) and expression of CD11b CD32 and CD64, it's involvement in the biology of M-MDSC was not explored previously, as the nomenclature and function of MDSCs didn't come into existence until 2007. VNN2 expression may mark an undifferentiated cell stage, with its expression present in self-renewing hematopoietic stem cells.

Here, we show that VNN2 is a surface protein enriched on M-MDSC that can be used to positively identify, quantify and isolate live human M-MDSC. In order to determine whether VNN2 was present in cells we currently classify as Mo-MDSC, we used flow cytometry to purify M-MDSC cells and compared VNN2 mRNA expression versus CD14$^+$ HLA-DR$^+$ monocytes by qPCR. Interestingly VNN2 mRNA was expressed 30-fold higher in M-MDSC compared to CD14$^+$ HLA-DR$^+$ monocytes and VNN2 protein expression on M-MDSC was 65% compared to only 3% in CD14$^+$ HLA-DR$^+$ cells (n=8 p<0.01). Analytic examination of the top 10% of VNN2-expressing CD14$^+$ (CD14$^+$ VNN2$^{high}$) cells by flow cytometry revealed expression of CD33$^+$ and CD11b$^+$ while CD3, CD15, CD19 and CD56 were all negative and HLA-DR was low, which is consistent with the phenotype of human M-MDSCs. Sorted CD14$^+$ VNN2$^{high}$ expressing monocytes inhibited proliferation of CD8 T cells in a manner comparable to the suppressive capacity of traditional Mo-MDSC at ~48% and 51% respectively. These results suggest that the most intense surface expression of the ectoenzyme VNN2 on CD14$^+$ cells selectively marks a subpopulation of monocytes consistent with a Mo-MDSCs phenotype and may be an alternative approach to positively identify, quantify and isolate functional live human Mo-MDSC.

Materials and Methods
Cell Isolation and Sorting

PBMC were isolated from freshly obtained healthy patients' blood by Histopaque density gradient centrifugation (Sigma-Aldrich, St. Louis, Mo.). CD14$^+$ monocytes were positively selected from PBMC using magnetic CD14 Micro beads (Miltenyi Biotech, San Diego, Calif.) with a magnet according to the manufacturer's instructions. CD14$^+$ cells were then flow-sorted into M-MDSC using a BD FACS Aria flow cytometer (BD, Franklin Lakes, N.J.). The purity of the M-MDSC cells after sorting was >93%.

Surface Staining and Flow Cytometric Analysis

To purify Mo-MDSC cells from PBMC, multi-color fluorescence-activated cell sorting was done using the following antibodies: anti-CD14-APC (Invitrogen, Carlsbad Calif.) and HLA-DR-FITC (BD Biosciences, San Jose, Calif.) during 30 min at 4° C. The following PE-conjugated mouse anti-human antibodies also were used to analyze cells: VNN2 (MBL, Woburn, Mass.), CD19 and CD56. CD3 was FITC conjugated (R&D Systems, Minneapolis Minn.). Analysis of FACS-data was done using Winlist software V7.0 (Verity, Topsham, Ma.). Isotype-matched antibodies were used with all the samples as controls.

Suppression Assay

M-MDSC cells were purified and sorted as described above. Autologous CD8 T cells were isolated from PBMC using anti-CD8 micro beads and a magnetic column (Miltenyi Biotech). CD14$^+$ VNN2$^+$ monocytes or Mo-MDSCs were seeded 2:1 in a 96-well round-bottom plate with CD8 cells previously labeled with 5 µM of e670 (eBiosciences, San Diego, Calif.). CD8 T cell proliferation was induced by anti-CD2/CD3/CD28 stimulation beads at a 1:16 ratio (Miltenyi Biotech) and the suppressive capacity of Mo-MDSCs was measured using a BD C6 flow cytometer after six days of co-culture at 37° C. in 5% $CO_2$. Controls included a positive T cell proliferation control (CD8 T cells alone) an induction negative control (CD8 T cells with medium only, data not shown) and labeled but un-stimulated CD8 cells (data not shown).

Statistical Analysis

The statistical significance between values was determined by Student's t test. All data were expressed as the mean±SEM. Probability values of p<0.05 were considered significant.

Results

VNN2 mRNA is Increased in Mo-MDSC Compared to CD14$^+$ HLA-DR$^+$ Monocytes

CD14$^+$ monocytes were positively selected from peripheral PBMCs and assessed for HLA-DR expression (FIG. 1A). M-MDSC (CD14$^+$ HLA-DR$^{low/neg}$) and CD14$^+$ HLA-DR$^+$ cells were sorted by flow cytometry and mRNA was extracted using a Qiagen RNA extraction kit (FIG. 1A). qPCR was performed using VNN2-specific primers and the mRNA expression of VNN2 was compared between M-MDSC versus CD14$^+$ HLA-DR$^+$ cells. As shown in FIG. 1B, VNN2 mRNA expression in M-MDSC was 30-fold higher compared to the VNN2 mRNA expression in CD14$^+$ HLA-DR$^+$ cells.

VNN2 Protein is Enriched in Mo-MDSC Compared to CD14+ HLADR$^+$ Monocytes

After detecting increased expression of VNN2 mRNA in human Mo-MDSC compared to CD14$^+$ HLA-DR$^+$ cells, we used flow cytometry to assess the level of VNN2 on the surface of Mo-MDSC compared to CD14$^+$ HLA-DR$^+$ monocytes. As shown in the representative FIG. 2A, VNN2 protein expression was enriched in Mo-MDSC compared to CD14$^+$ HLA-DR$^+$ cells based upon isotype for VNN2 expression. Repeating the assay demonstrates that a significant difference in VNN2 expression can be observed between Mo-MDSC and CD14$^+$HLA-DR$^+$ monocytes (FIG. 2B, p<0.000001, n=8). Next, using flow cytometry, we compared the surface expression of HLA-DR on the top 10% of VNN2-expressing CD14$^+$ cells (CD14$^+$VNN2$^{high}$) to the bottom 10% of VNN2-expressing CD14$^+$ cells (CD14$^+$VNN2$^{low}$). As FIG. 2C shows, compared to isotype controls, among CD14$^+$VNN2$^{high}$ cells, only 13% expressed HLA-DR above isotype, whereas among CD14$^+$VNN2$^{low}$ cells greater than 79% expressed HLA-DR staining above isotype levels. Cumulative data for HLA-DR expression among CD14$^+$VNN2$^{high}$ shows an average of 31% HLA-DR expression whereas, HLA-DR expression among CD14$^+$ VNN2$^{low}$ cells was 92% (FIG. 2D)

CD14$^+$ VNN2$^{high}$ Cells are CD11b$^+$ CD33$^+$ CD3$^{neg}$ CD15$^{neg}$ CD19$^{neg}$ and CD56$^{neg}$ Total positively selected CD14$^+$ cells were stained with antibodies specific for bona fide M-MDSC surface markers. One hundred percent of the CD14$^+$ cells were positive for CD33 and CD11b (FIGS. 3A&B), while negative for CD15. Whereas the CD14$^+$VNN2$^{high}$ subset of CD14$^+$ cells were negative for CD19, CD56 and CD3 (FIGS. 3C, D, E & F), consistent with what is known regarding human M-MDSC markers. Expression of M-MDSC markers among the CD14$^+$VNN2$^{low}$ population was negative for all markers examined.

CD14$^+$VNN2$^{high}$ Monocytes Suppress CD8 T Cell Proliferation at Levels Similar to Traditional CD14$^+$ HLA-DR$^{neg/low}$ Mo-MDSC Next, we performed an in vitro suppressive assay which has been described as the ultimate determinant in order to establish the definitive identity and functional capacity of M-MDSC. As shown in FIG. 4A, CD14$^+$VNN2$^{high}$ cells were sorted and mixed at a 2:1 in a 96-well round-bottom plate with CD8 cells previously labeled with e670 (eBiosciences, San Diego, Calif.) and stimulated by anti-CD2/CD3/CD28 beads at a 1:16 ratio (Miltenyi Biotech). The suppressive capacity of M-MDSCs was measured using a BD C6 flow cytometer after six days of co-culture at 37° C. in 5% CO2 and 37° C. Compared to traditional Mo-MDSC (CD14$^+$HLA-DR$^{low/neg}$) (FIG. 4A, panel III, the CD14$^+$ VNN2$^{high}$ cells (FIG. 4A, panel II) suppressed proliferating CD8 T cells at a very similar range. Neither the CD14$^+$ VNN2$^{low}$ cells nor CD14$^+$HLA-DR$^+$ monocytes effectively suppressed CD8 T cell proliferation (FIG. 4A, panels IV and V, respectively). Cumulative data demonstrated a consistent suppressive capacity for expressing CD14$^+$ VNN2$^{high}$ cells comparable to traditionally sorted M-MDSC (FIG. 4B, p>0.05, n=8, panels II vs. III). A similar result showed no significant differences between CD14$^+$VNN2$^{low}$ cells and CD14$^+$ HLA-DR$^+$ monocytes (FIG. 4B, p>0.05, n=8, panels IV vs. V).

CD14$^+$VNN2$^{high}$ Monocytes are Increased in Renal Metastatic Cancer

M-MDSCs have been described to be increased in the peripheral blood of several malignancies. In order to further assess the equivalence of CD14$^+$VNN2$^{high}$ cells to traditionally identified Mo-MDSC, we determined the presence of CD14$^+$ VNN2$^{high}$ in stage IV renal metastatic cancer patients. As shown in FIG. 5A, CD14$^+$VNN2$^{high}$ cells were increased in renal metastatic cancer (RCC) patients (top right panel) based on isotype control expression of VNN2 (25%) compared to healthy controls (bottom right panel, 13%). Cumulative data demonstrates a near two-fold increase in CD14$^+$VNN2$^{high}$ cells among RCC patients (FIG. 5B).

Example 2

RNA Array Comparison Between Flow Cytometry-Purified Common Monocytes (CD14+ HLA-DR$^{high}$) vs M-MDSC (CD14+ HLA-DR$^{negative}$)

Two types of MDSC are currently recognized: monocytic (M-MDSC) and granulocytic (GMDSC). M-MDSC are identified based on surface expression of the gene CD14 and lack of the gene HLA-DR (therefore in scientific literature these cells are designated CD14positive and HLA-DRnegative or CD14+ HLA-DRneg for abbreviation purposes). However, these genes are recognized to NOT be specific enough and a good set of MDSC-specific genes to identification these cells precisely is sought in the clinical and scientific community.

Results

We undertook an RNA array comparison between flow cytometry-purified common monocytes (CD14+ HLA-DR$^{high}$) vs M-MDSC (CD14+ HLA-DR$^{negative}$) in order to identify differentially over-expressed genes in M-MDSC cells.

The results of this array identified 27 genes that are elevated in M-MDSC compared to CD14+ HLA-DR$^{high}$ monocytes. As summarized in FIG. 6, we have validated the upregulation of 25 genes by quantitative PCR—qPCR-. Further, we have used the surface markers identified in this assay as the source for selection of M-MDSC in a live assay and demonstrated that MMDSCs selected in this manner are suppressive using functional assays established in our lab. Therefore, from the 25 qPCR validated genes, we have further narrow the results to unique 24 genes. The final candidate genes so far are listed in the Table 1.

TABLE 1

| VNN2 | FCAR | SERPINB10 |
| KCNJ15 | TSHZ3 | CLEC4D |
| SERPINB2 | NRG1 | TREM1 |
| CREB5 | ALOX5AP | CLEC4E |
| ICAM3 | PADI4 | CD82 |
| NFE2 | PADI2 | MGAM |
| MNDA | QPC | TMEM45B |

Example 3

Figure 7:
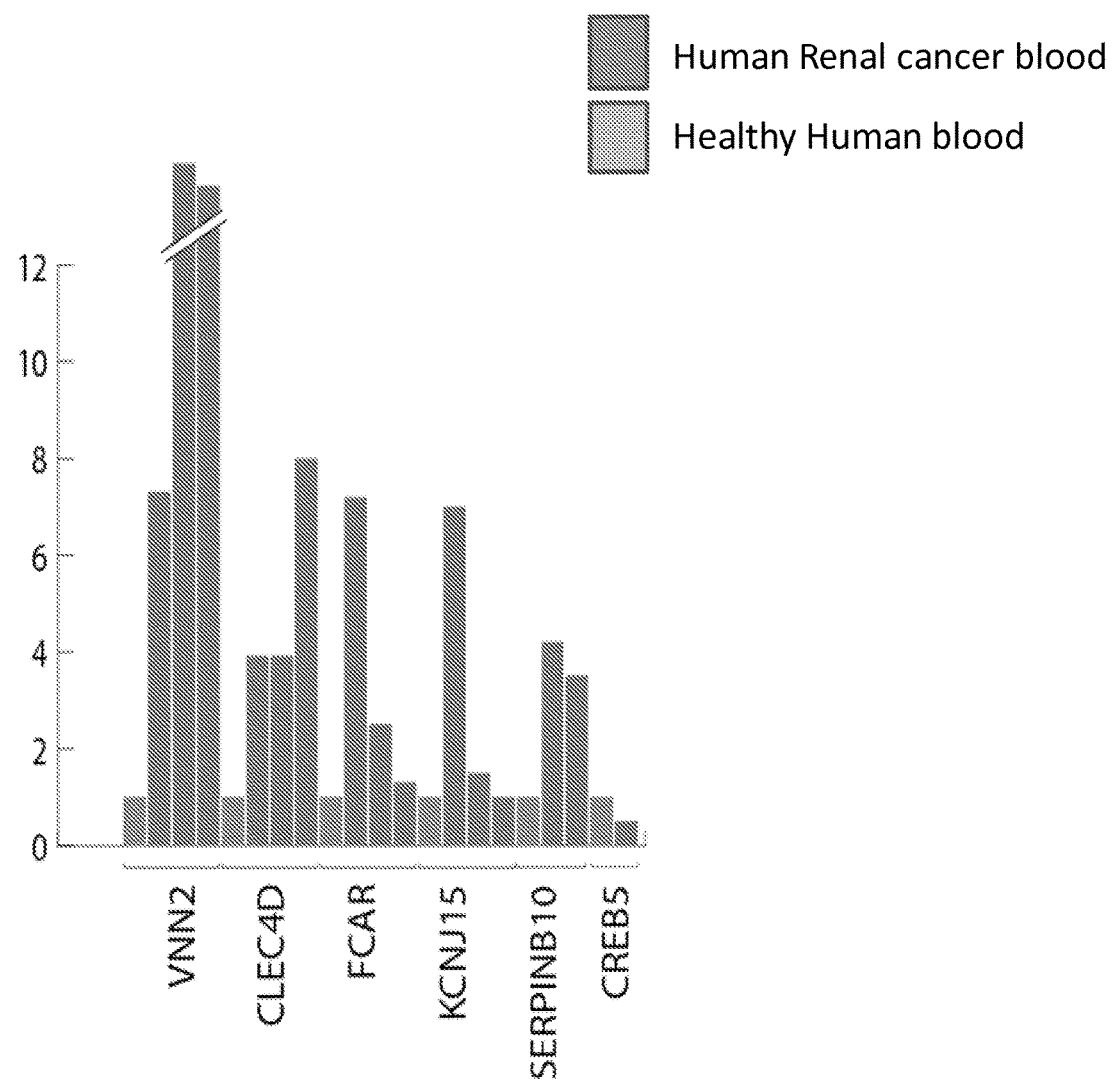
FIG. 7 is a bar graph illustrating the clinical application of whole blood-based cancer detection by qPCR in a subject with renal cancer compared to a healthy control subject. RNA is extracted from lysed whole blood samples and reverse-transcribed into cDNA. qPCR was applied using specific primers for VNN2, CLEC4D, CD89 (FCAR), KCNJ15, SERPINB10 and CREB5. Values obtained from renal cancer blood qPCR and values obtained from normal blood qPCR are shown.
Figure 8:
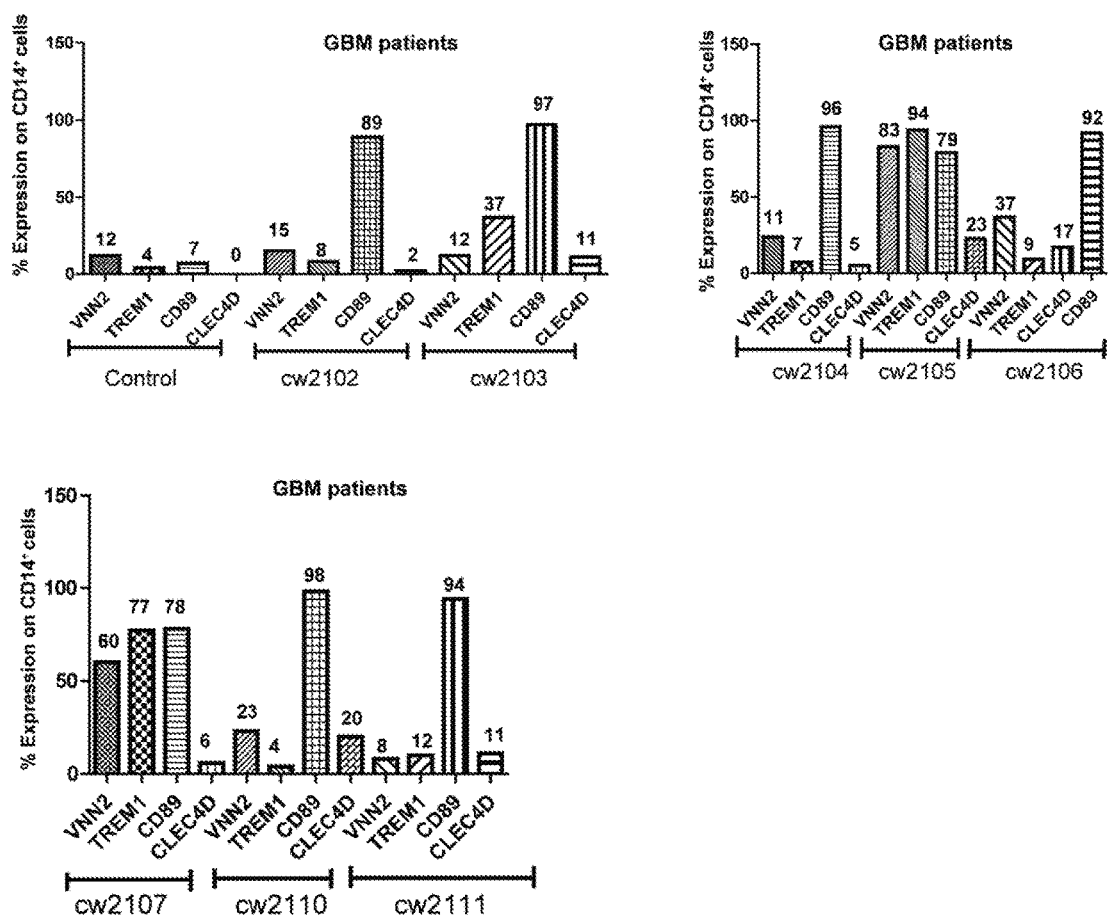
FIG. 8 is a bar graph illustrating the upregulation of VNN2, TREM1, CD89 (FCAR), and CLEC4D biomarkers in 8 patients with glioblastoma cancer compared to a control.

Clinical Application of Whole Blood-Based Cancer Detection by qPCR Protocol Used for Renal Cancer Blood Sample 5 mL of heparinized human whole blood were lysed 10' with ACK lysis buffer (Invitrogen, Calif.) and centrifuged 1500 rpm 7' at 4° C. This procedure was repeated one more time and then the RNA from the cell pellet was extracted using Qiagen RNA extraction kit following the manufacturer's instructions. 100 ng of the mRNA was then reverse transcribed into cDNA using SuperScript III First Strand kit following manufacturer's instruction (Invitrogen, Calif.) Quantitative PCR (qPCR) was performed in triplicates for each gene target (TABLE 2) using 10 ng of cDNA per well in a StepOne Plus Real-Time PCR System (Life Technologies, NY). 18S was used as the endogenous control. Renal Cancer patient results were then compared to control qPCR results using StepOne Software (Life Technologies, NY) as shown in FIG. 7.

TABLE 2

| VNN2 | CLEC4D | FCAR |
| KCNJ15 | SerpinB10 | CREB5 |

Having described the invention, the following is claimed:

1. A method of determining the efficacy of a cancer therapeutic which affects M-MDSC mediated immunosuppression in treating a cancer and treating the cancer in a subject, the method comprising:
administering a first amount of the cancer therapeutic agent to the subject, wherein the first amount is the amount effective to modulate a level of two or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3 in the subject;

obtaining a blood sample from the subject;

determining, in the blood sample, the level of two or more of the polypeptides selected from the group consisting of VNN2, KCNJ15, SERPINB2, CREB5, ICAM3, NFE2, MNDA, PXN, FCAR, TSHZ3, NRG1, ALOX5AP, PAD14, PAD12, QPC, VNN1, SERPINB10, CLEC4D, TREM1, CLEC4E, CD82, MGAM, TMEM45B and VNN3; and administering a second amount of the cancer therapeutic agent if the level of two or more of the polypeptides compared to a control level is decreased, wherein the second amount is the amount effective to reduce M-MDSC mediated imunnosuppresion in the subject.

2. The method of claim 1, wherein a decrease in the level of two or more of the polypeptides compared to a control level is indicative of a decrease in the level of M-MDSCs in the subject.

3. The method of claim 1, wherein the level of the two or more polypeptides is determined using an immunoassay selective for the two or more of the polypeptides.

4. The method of claim 1, wherein the level of the two or more polypeptides is determined using a hybridization assay.

5. The method of claim 1, wherein the blood sample is a whole blood sample.

6. The method of claim 1, the cancer selected from renal, prostate, or glioblastoma cancer.

7. The method of claim 1, administering the second amount of the cancer therapeutic if the level of two or more of the polypeptides selected from VNN2, CLEC4D, CD82, CD89, ICAM3, KCNJ15 and TREM1 compared to a control level is decreased.

* * * * *